United States Patent
Wershofen et al.

(10) Patent No.: US 10,759,736 B2
(45) Date of Patent: Sep. 1, 2020

(54) PROCESS FOR THE PREPARATION OF DI- AND POLYAMINES OF THE DIPHENYLMETHANE SERIES

(71) Applicant: COVESTRO DEUTSCHLAND AG, Leverkusen (DE)

(72) Inventors: Stefan Wershofen, Mönchengladbach (DE); Richard Adamson, Leichlingen (DE); Georg Pirkl, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/598,170

(22) Filed: Oct. 10, 2019

(65) Prior Publication Data

US 2020/0123096 A1    Apr. 23, 2020

(30) Foreign Application Priority Data

Oct. 17, 2018   (EP) .................................... 18200855

(51) Int. Cl.
  *C07C 209/78*   (2006.01)
  *C07C 209/86*   (2006.01)

(52) U.S. Cl.
  CPC .......... *C07C 209/78* (2013.01); *C07C 209/86* (2013.01)

(58) Field of Classification Search
  None
  See application file for complete search history.

(56) References Cited

U.S. PATENT DOCUMENTS

| | | | |
|---|---|---|---|
| 3,576,875 | A | 4/1971 | Rohe |
| 4,034,039 | A | 7/1977 | Sun |
| 4,201,722 | A | 5/1980 | Sun |
| 5,310,769 | A | 5/1994 | Konig |

(Continued)

FOREIGN PATENT DOCUMENTS

| | | |
|---|---|---|
| DE | 19804918 A | 8/1999 |
| DE | 10031540 A1 | 1/2002 |

(Continued)

OTHER PUBLICATIONS

European Search Report, EP 18200855, dated Mar. 11, 2019.

*Primary Examiner* — Amy C Bonaparte
(74) *Attorney, Agent, or Firm* — Donald R. Palladino

(57) ABSTRACT

The invention relates to a process for the preparation of di- and polyamines of the diphenylmethane series (MDA), in which firstly crude MDA is prepared and is then subjected to a distillation process, wherein the distillation process comprises the following:
  in a distillation column, separating off a stream containing aniline and water as head product so as to obtain the first product stream as sump product,
  in said distillation column or in an apparatus arranged downstream of said distillation column, performing a stripping with steam so as to obtain a gaseous stream containing aniline, water and MMDA,
  partially condensing this gaseous stream containing aniline, water and MMDA so as to obtain a liquid stream containing MMDA and water (and optionally aniline) and a gaseous stream containing aniline and water (and optionally MMDA),
  drying the liquid stream containing MMDA and water (and optionally aniline) obtained by the partial condensation so as to obtain the second product stream.

15 Claims, 4 Drawing Sheets

(56) References Cited

U.S. PATENT DOCUMENTS

| | | |
|---|---|---|
| 5,312,989 A | 5/1994 | Yamamoto |
| 2004/0092701 A1 | 5/2004 | Koch et al. |
| 2006/0094897 A1 | 5/2006 | Muller et al. |
| 2006/0224018 A1 | 10/2006 | Hagen et al. |
| 2007/0179316 A1 | 8/2007 | Pohl et al. |
| 2007/0179317 A1 | 8/2007 | Keggenhoff et al. |
| 2008/0200721 A1 | 8/2008 | Muller et al. |
| 2009/0005596 A1 | 1/2009 | Bock et al. |
| 2010/0036154 A1 | 2/2010 | Michalczak et al. |
| 2011/0028755 A1 | 2/2011 | Grund et al. |

FOREIGN PATENT DOCUMENTS

| | | | |
|---|---|---|---|
| DE | 202013003950 | * | 6/2013 |
| EP | 31423 A | | 7/1981 |
| EP | 934922 B1 | | 8/1999 |
| EP | 1167343 B1 | | 5/2003 |
| GB | 1287192 A | | 8/1972 |
| GB | 1517585 A | | 7/1978 |
| JP | 2004026753 A | | 1/2004 |
| RO | 104327 B1 | | 12/1993 |
| SU | 463658 A | | 3/1975 |

\* cited by examiner

PROCESS FOR THE PREPARATION OF DI- AND POLYAMINES OF THE DIPHENYLMETHANE SERIES

CROSS-REFERENCE TO RELATED APPLICATION

This application claims priority to European Application No. 18200855.7, filed Oct. 17, 2018, which is incorporated herein by reference.

FIELD

The invention relates to a process for the preparation of di- and polyamines of the diphenylmethane series (MDA), in which firstly crude MDA is prepared and is then subjected to a distillation process, wherein the distillation process comprises the following:
- in a distillation column, separating off a stream containing aniline and water as head product so as to obtain the first product stream as sump product,
- in said distillation column or in an apparatus arranged downstream of said distillation column, performing a stripping with steam so as to obtain a gaseous stream containing aniline, water and MMDA,
- partially condensing this gaseous stream containing aniline, water and MMDA so as to obtain a liquid stream containing MMDA and water (and optionally aniline) and a gaseous stream containing aniline and water (and optionally MMDA),
- drying the liquid stream containing MMDA and water (and optionally aniline) obtained by the partial condensation so as to obtain the second product stream.

BACKGROUND

Di- and polyamines of the diphenylmethane series are important starting materials for the preparation of the corresponding isocyanates. These are in turn prepared in large amounts and in particular are used for the preparation of polyurethanes. The industrial preparation of these isocyanates has been described many times in the literature and is achieved in particular by reacting the corresponding amines with phosgene in a solvent. In the sense of the present invention di- and polyamines of the diphenylmethane series are understood to mean amines and mixtures of amines of the following type:

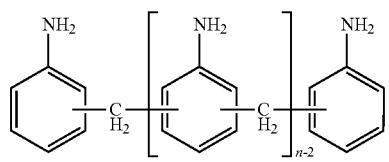

(I)

Here, n stands for a natural number≥2. Hereinafter, the compounds of this type in which n=2 shall be referred to as diamines of the diphenylmethane series or diaminodiphenylmethane (hereinafter MMDA). Compounds of this type in which n>2 shall be referred to within the scope of this invention as polyamines of the diphenylmethane series or polyphenylenepolymethylene polyamines (hereinafter PMDA). Mixtures of both types shall be referred to as di- and polyamines of the diphenylmethane series (hereinafter MDA). The corresponding isocyanates, which can be derived formally by replacing all $NH_2$ groups by NCO groups from the compounds of formula (I) shall be accordingly referred to as diisocyanates of the diphenylmethane series (hereinafter MMDI), polyisocyanates of the diphenylmethane series or polyphenylenepolymethylene polyisocyanates (hereinafter PMDI) or di- and polyisocyanates of the diphenylmethane series (subsequently MDI). Here, both in the case of the amine and also in the case of the isocyanate, the polymer (n>2) is generally always present in the mixture with the difunctional compound (n=2), and therefore in practice only two compound types are relevant: the pure diamines or diisocyanates (MMDA or MMDI) on the one hand and the mixture of difunctional compound and the polymer (MDA or MDI) on the other hand. Within the scope of the present invention streams of the amines or isocyanates shall be referred to as "pure" difunctional compounds (MMDA or MMDI) if the mass fraction of the difunctional compounds is at least 95.0% in relation to the total mass of the stream in question.

MDA is usually prepared by acid catalyzed reaction of aniline with formaldehyde with subsequent neutralization and preparation of the reaction product. The continuous, discontinuous or semi-continuous preparation of di- and polyamines of the diphenylmethane series is described in numerous publications and patents (for example EP-A-31 423; EP 934 922 B1; EP-B-1 167 343; EP-A-1 403 242; EP-A-1 707 557; EP-A-1 813 597; EP-A-1 813 598; U.S. Pat. No. 5,310,769; DE-A-198 04 918; JP-A-2004026753). The MDA obtained as reaction product contains substantially MMDA (as a mixture of the three technically notable MMDA isomers 4,4'-diaminodiphenylmethane, 2,4'-diaminodiphenylmethane and 2,2'-diaminodiphenylmethane) and the corresponding higher-nuclear PMDA homologues and PMDA isomers. In addition, numerous secondary products and trace components are also contained in the MDA in very different fractions. In particular, crude MDA does routinely contain unreacted aniline and water. Their separation to less than 1000 ppm (aniline) or less than 200 ppm (water) by an at least two-step distillation process comprising a flash evaporation and subsequent cooling is described in EP-A-1 813 597.

The main use of MDA is the aforementioned preparation of the corresponding isocyanate. In most industrial processes the MDA is phosgenated directly into MDI; i.e. the MDA as obtained in the acid catalyzed condensation of aniline and formaldehyde (without separation into its isomers or homologues) is subjected to phosgenation. Only at the isocyanate stage does separation occur into the diisocyanate (MMDI) and a mixture of MMDI and PMDI, the MMDI fraction being reduced in relation to the crude product in accordance with the amount of the diisocyanate separated off.

For certain fields of application, for example as a crosslinker in plastics or varnishes, the amine itself may also be used, whether in the form of the aforedescribed mixture of isomers and homologues (MDA) or in the form of the diamine (MMDA). In addition, ring hydrogenation, in particular for the preparation of the ring-hydrogenated diamine ($H_{12}$-MMDA, diaminodicyclohexylmethane), is known (see for example WO 2009/144148 A1, WO 2008/077672 A1). $H_{12}$-MMDA for its part can be converted by means of phosgenation or via alternative processes into the corresponding isocyanate ($H_{12}$-MMDI, dicyclohexylmethane diisocyanate) (see for example WO 2009/144148 A1, WO 2008/077672 A1). For many such fields of application not relating to the preparation of MDI, it is desirable to have the diamine (MMDA) available in the greatest purity possible, i.e. with the smallest possible fraction of polymers.

In addition, pure MMDA, in contrast to MDA (which in the terminology of the present invention always contains substantial fractions of higher homologues that can only be evaporated with difficulty) can be phosgenated without problem in the gas phase into MMDI, such that it is possible to make use of the advantages of gas-phase phosgenation known from the preparation of toluene diisocyanate (TDI).

A series of processes for the separation of MMDA from MDA are known from the prior art:

Thus, MMDA can be separated off and the pure state of the 4,4'-MMDA can be isolated by means of extraction, as described for example in SU 463 658, by means of reaction with metal salts, as described in GB 1 169 127, by melting, as described in EP-A-0 572 030, or by treatment with solvents, as described in BE 855 402 and U.S. Pat. No. 4,034,039.

RO 104327 B1 describes the separation of MMDA by means of thin-film distillation. It is also known to separate off MMDA from MDA by means of distillation.

DE-OS-1 901 993 describes a process for the preparation of 4,4'-MMDA, in which the MMDA is distilled off from a mixture of MMDA and PMDA and then 4,4'-MMDA is separated off by crystallization. The distillation is performed at 2 Torr and 220 to 230° C.

DE-OS-100 31 540 describes a process for separating off 2,2'-MMDA and 2,4'-MMDA from MDA. To this end, a distillation column having at least 40 separation stages can be used. The distillation is performed with a temperature profile of from 180 to 280° C., at a head pressure of from 0.1 to 10 mbar, and at a sump pressure of from 8 to 20 mbar. Fabric packing that has a low pressure loss is used in order to reduce the pressure losses. The MDA freed of 2,2'- and 2,4'-MMDA is reacted with phosgene to form MDI; the separated-off 2,2'- and 2,4'-MMDA is fed back into the condensation stage.

WO 2006/103189 A1 describes the preparation of MDA, separation of same into a partial stream containing substantially MMDA and a partial stream containing the remaining MMDA and PMDA, and separate phosgenation of the two partial streams. The partial stream containing substantially MMDA is phosgenated in the gas phase and the partial stream containing the remaining MMDA and PMDA is phosgenated in the liquid phase. The separation of the two amine partial streams is preferably performed with distillation, for example in two successive distillation columns or in a dividing wall column, wherein in the case of the latter embodiment the partial stream consisting substantially of MMDA is removed in a side drain of the dividing wall column.

Separation of 4,4'-MMDA by distillation is described in WO 2007/085534 A1, wherein the MDA is divided into two partial streams. The first partial stream is for example divided into a main stream containing substantially 4,4'-MMDA, a sump stream and a head stream in two successive columns or in a dividing wall column. The sump stream and head stream are combined again with the second partial stream and are used for example as starting material for phosgenation to form MDI.

A disadvantage of all previous processes for separating off MMDA and/or for the separation of the MMDA isomers is that a separate process requiring a complex equipment set-up is necessary (for example two-stage distillation or the use of a dividing wall column, which is difficult to control), in which the secondary products which are created usually have to be disposed of. In addition, the use for example of a separate distillation stage may lead to a reduction in the quality of the obtained MDA and the MDI prepared therefrom due to the increased thermal load.

There was thus a need for a process which makes it possible to recover MMDA from MDA with a high level of purity, i.e. in particular with a minimal fraction of PMDA, without having to exert a high process (distillation) effort. In particular, the process should be suitable for integration in the simplest manner possible into existing plants for the production of MDA, and, once the MMDA has been separated off, the remaining MDA (with a necessarily reduced MMDA fraction) should also be suitable for the usual uses of MDA.

SUMMARY

Taking into account the above, one subject of the present invention is a process, as described hereinafter, for the preparation of di- and polyamines of the diphenylmethane series. The references between parentheses starting with "X" refer to the appended drawings FIG. 1 to FIG. 7, where "X" stands for the number of the drawing. The process according to the invention comprises the steps:

a) subjecting aniline and formaldehyde to acid catalyzed condensation so as to obtain an acidic process product containing water, di- and polyamines of the diphenylmethane series (MDA), and aniline;

b) neutralizing the process product obtained in step a) followed by separation into an organic phase containing MDA and aniline and an aqueous phase;

c) optionally (and preferably), washing the organic phase containing MDA and aniline obtained in step b);

d) distilling the organic phase (X01) containing MDA and aniline obtained in step b) or step c) so as to obtain a first product stream (X02) containing, in relation to its total mass, at least 25.0 mass-%, preferably 30.0 mass-% to 70.0 mass-%, and particularly preferably 35.0 mass-% to 65.0 mass-% of polyamines of the diphenylmethane series (PMDA), wherein the remainder to 100 mass-% consists at least of the diamines of the diphenylmethane series (MMDA), and a second product stream (X10) containing, in relation to its total mass, at least 95.0 mass-% (i.e. 95.0 mass-% to 100 mass-%, in particular 95.0 mass-% to 99.999 mass-%), preferably at least 97.0 mass-%, particularly preferably at least 98.0 mass-% of diamines of the diphenylmethane series (MMDA), the process comprising the steps in a distillation column, separating off a stream (X03) containing aniline and water as head product so as to obtain the first product stream (X02) as sump product, in said distillation column or in an apparatus arranged downstream of said distillation column, performing a stripping with steam so as to obtain a gaseous stream containing aniline, water and MMDA, partially condensing the gaseous stream containing aniline, water and MMDA obtained by the stripping with steam (X05) so as to obtain a liquid stream containing MMDA and water (and optionally aniline) and a gaseous stream containing aniline and water (and optionally MMDA), drying, in particular by stripping with an inert gas (X09) (preferably nitrogen) under heating, the liquid stream containing MMDA and water (and optionally aniline) obtained by the partial condensation, in particular followed by a cooling, so as to obtain the second product stream (X10).

BRIEF DESCRIPTION OF THE DRAWINGS

Various features and characteristics of the inventions described in this specification may be better understood by reference to the accompanying figures, in which.

DETAILED DESCRIPTION

Figure 1:
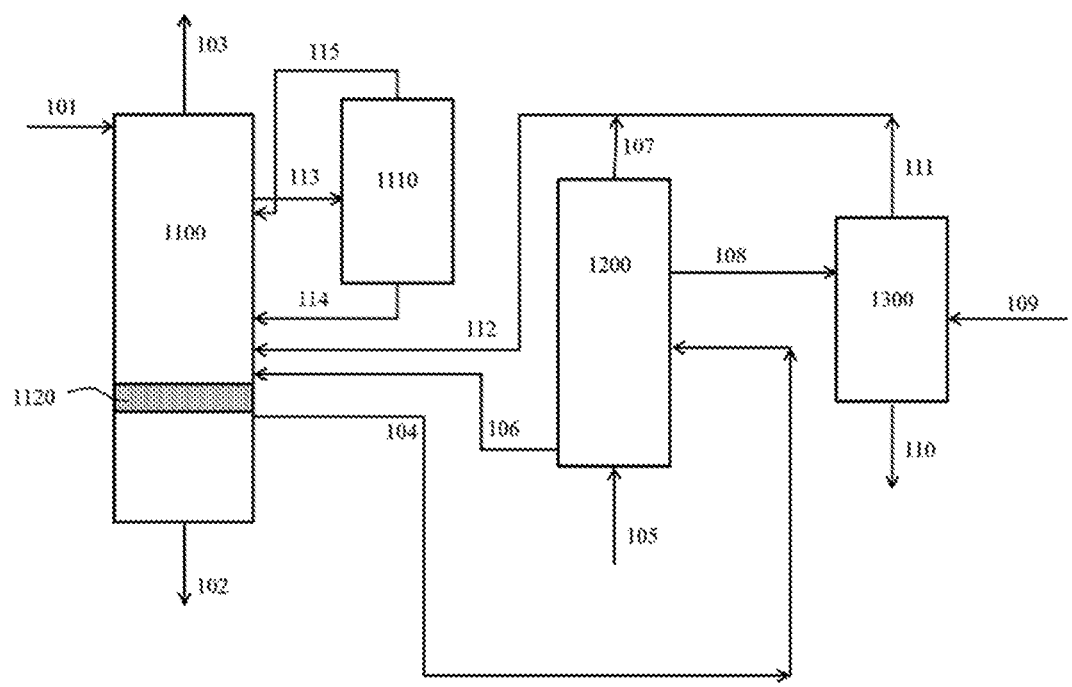
FIG. 1 shows a possible embodiment of the process according to the invention with two distillation steps in the distillation columns 1100 and 1200.

In the sense of the present invention "stripping" means a physical separation process in which the substance mixture to be separated is brought into contact with a gas (the "stripping gas") so as to support the separation process. In step d) according to the invention the separation of aniline and water is supported by stripping with steam as stripping gas. This stripping with steam takes place in accordance with the invention either in the distillation column, in which the first product stream (X02) is also obtained (by introducing steam into this distillation column), or in an "apparatus arranged downstream of this distillation column". Here, the expression "arranged downstream" means that both pieces of equipment are connected to one another such that an outlet stream from the distillation column is an inflow stream of said apparatus for steam stripping. To this end it is preferred, as also described in greater detail further below with reference to examples of specific positioning possibilities of the column, to connect the apparatus for steam stripping to a side drain of the distillation column, optionally via further pieces of equipment connected in between, such as in particular an evaporator. It is also possible to guide a part of the sump stream of the distillation column into the apparatus for steam stripping. Suitable apparatuses for stripping with steam are known to a person skilled in the art (stripping columns, in particular packed columns, for example columns with random packing or columns with structured packing).

The second product stream (X10) containing "at least 95.0 mass-%, preferably at least 97.0 mass-%, particularly preferably at least 98.0 mass-% of diamines of the diphenylmethane series (MMDA)" may contain not only MMDA, but in particular also small fractions of PMDA as well as non-reacted aniline, water and optionally secondary components.

A brief summary of various possible embodiments of the invention will now be provided.

In a first embodiment of the invention, which can be combined with all other embodiments, the first product stream contains 30.0 mass-% to 70.0 mass-% of polyamines of the diphenylmethane series, and the second product stream contains at least 97.0 mass-% of diamines of the diphenylmethane series.

In a second embodiment of the invention, which is a particular variant of the first embodiment, the first product stream contains 35.0 mass-% to 65.0 mass-% of polyamines of the diphenylmethane series, and the second product stream contains at least 98.0 mass-% of diamines of the diphenylmethane series.

In a third embodiment of the invention, which can be combined with all other embodiments, a molar ratio of the total aniline used to the total formaldehyde used of 1.6 or more is used in step a).

In a fourth embodiment of the invention, which can be combined with all other embodiments, step c) is included.

In a fifth embodiment of the invention, which can be combined with all other embodiments, the stripping with steam is performed in the distillation column.

In a sixth embodiment of the invention, which is an alternative to the fifth embodiment and otherwise can be combined with all other embodiments, the stripping with steam is performed in an apparatus arranged downstream of the distillation column.

In a seventh embodiment of the invention, which is a particular variant of the sixth embodiment, a packed column is used as apparatus arranged downstream of the distillation column.

In an eighth embodiment of the invention, which is a particular variant of the sixth and seventh embodiment, the apparatus arranged downstream of the distillation column is connected to a side drain of the distillation column, optionally via an intermediate piece of equipment.

In a ninth embodiment of the invention, which is a particular variant of the eighth embodiment, a piece of equipment is connected between the distillation column and the apparatus.

In a tenth embodiment of the invention, which is a particular variant of the ninth embodiment, the piece of equipment is an evaporator.

In an eleventh embodiment of the invention, which is a particular variant of the sixth and seventh embodiment, some of the sump product of the distillation column is conducted into the apparatus arranged downstream of the distillation column.

In a twelfth embodiment of the invention, which can be combined with all other embodiments, the drying in step d) is performed by stripping with an inert gas under heating.

In a thirteenth embodiment of the invention, which is a particular variant of the twelfth embodiment, a cooling is performed in step d) after the drying.

The embodiments described in brief above and further possible variants of the invention will be explained in greater detail hereinafter. The embodiments can be combined arbitrarily with one another, unless otherwise evident from the context.

In step a) of the process according to the invention aniline and formaldehyde are reacted to form MDA with use of acid catalysts. Due to the variation in the molar ratio of acid to aniline (degree of protonation) and of aniline to formaldehyde (A/F ratio), the fraction of the MMDA and the isomer composition in the MDA can be set within broad ranges. In accordance with the invention the reaction in step a) is performed such that not all aniline reacts, but instead some of the aniline is not reacted. Thus, within the scope of the present invention, a molar ratio of total used aniline to total used formaldehyde equal to or greater than 1.6 is preferably selected. (Stoichiometrically, a molar ratio of total used aniline to total used formaldehyde of 2.0 is required to form the diamine; in the case of the polyamines the ratio is less than 2.0. The molar ratio of total used aniline to total used formaldehyde is preferably at most 20.)

Formaldehyde is preferably used in the form of a 20% to 60% aqueous solution, in relation to the total mass of the formaldehyde solution. However, other formaldehyde sources, such as paraformaldehyde, trioxane or gaseous formaldehyde, can also be used, in principle. Formaldehyde can therefore be added to the process according to the invention in the form of monomeric formaldehyde and/or in the form of higher homologues (what are known as poly(oxymethylene) glycols). Brønstedt acids are usually used as catalysts. The use of HCl, either as gaseous hydrogen chloride (which is absorbed in aniline) or as hydrochloric acid, particularly preferably 15% to 36% hydrochloric acid in relation to the total mass of the hydrochloric acid, is preferred. In principle, other acids can also be used as homogeneous catalysts, as described in the literature references cited at the outset. The use of heterogeneous catalysts containing acidic centres is likewise possible.

In a first variant of step a) aniline is firstly brought to reaction with formaldehyde in the absence of an acid catalyst, then the aqueous phase is separated off, and the organic phase is mixed with the acid catalyst. During this process the aniline is firstly reacted with formaldehyde in a molar ratio of aniline:formaldehyde of at least 1.6:1, preferably 2.1:1 to 20:1, particularly preferably from 2.1:1 to 4.0:1, and at a temperature of preferably from 10° C. to 150° C., particularly preferably from 75° C. to 110° C. The acid catalyst is then added to the organic phase in a molar ratio of aniline:acid catalyst of from preferably 2.0:1 to 100:1 (corresponding to a degree of protonation of the aniline of from 50% to 1.0%), particularly preferably 4.0:1 to 20:1, at a temperature of from preferably 10° C. to 150° C., particularly preferably from 35° C. to 75° C. Hydrochloric acid, particularly preferably 15% to 36% hydrochloric acid, in relation to the total mass of hydrochloric acid, is preferably used as acid catalyst. The further reaction to complete the reaction is performed in a temperature range of from 20° C. to 220° C., preferably from 35° C. to 180° C.

In a second variant of step a) aniline and acid catalyst are firstly mixed, before formaldehyde is added. The acid catalyst is added to the aniline in a molar ratio of aniline:acid catalyst of from preferably 2.0:1 to 100:1 (corresponding to a degree of protonation of the aniline of from 50 to 1.0%), particularly preferably 4.0:1 to 20:1, at a temperature of from preferably 10° C. to 150° C., particularly preferably from 30° C. to 100° C. Hydrochloric acid, particularly preferably 15% to 36% hydrochloric acid, in relation to the total mass of hydrochloric acid, is preferably used as acid catalyst. The reaction mixture is then firstly reacted with formaldehyde in a molar ratio of from at least 1.6:1, preferably 2.1:1 to 20:1, particularly preferably from 2.1:1 to 4.0:1, and at a temperature of from preferably 10° C. to 150° C., particularly preferably 30° C. to 140° C., very particularly preferably 35° C. to 75° C. The further reaction to complete the reaction is performed in a temperature range of from 20° C. to 220° C., preferably from 35° C. to 180° C.

In a third variant of step a) a first partial amount of the aniline is reacted with the formaldehyde (for example as aqueous solution) and the aqueous phase is separated from the organic phase, and a second partial amount of the aniline is mixed with the acid catalyst (for example hydrochloric acid) before it is combined with the mentioned organic phase. The first partial amount of aniline is firstly reacted with formaldehyde in a molar ratio of aniline:formaldehyde of from preferably 1.4:1 to 20:1, particularly preferably from 1.4:1 and 4.0:1, and at a temperature of preferably from 10° C. to 150° C., particularly preferably from 75° C. to 110° C. The acid catalyst is added to the second partial amount of aniline in a molar ratio of aniline:acid catalyst of from preferably 0.5:1 to 10:1 (corresponding to a degree of protonation of the aniline of from 200% to 10%), particularly preferably 1.0:1 to 5:1, at a temperature of from preferably 10° C. to 150° C., particularly preferably from 30° C. to 100° C. Hydrochloric acid, particularly preferably 15% to 36% hydrochloric acid, in relation to the total mass of hydrochloric acid, is preferably used as acid catalyst. The organic phase obtained following the reaction of the first partial amount of the aniline with the formaldehyde is then combined with the second partial amount of the aniline containing the acid catalyst at a temperature of from preferably 10° C. to 150° C., particularly preferably 35° C. to 75° C. At this point of the reaction the molar ratio of aniline:formaldehyde is 1.6:1 to 20:1, particularly preferably from 2.1:1 to 4.0:1, and the molar ratio of aniline:acid catalyst is preferably 2.0:1 to 100:1 (corresponding to a degree of protonation of the aniline of from 50% to 1.0%), particularly preferably 4.0:1 to 20:1. The further reaction to complete the reaction is performed in a temperature range of from 20° C. to 220° C., preferably from 35° C. to 180° C.

Suitable mixing apparatuses for thoroughly mixing the reactants and catalyst are, for example, mixing pumps, jets or static agitators. Furthermore, the reactants are reacted in a suitable reaction apparatus, for example in tube reactors, stirred reactors, and reaction columns, or combinations thereof.

Usually, the reaction is performed without the use of a further solvent. Used as reaction medium is (excess) aniline and the water contained in the reaction mixture. The reaction of aniline with formaldehyde can be performed both continuously and discontinuously, in a batch or semibatch process.

The MDA-containing process product obtained in step a) contains, in relation to the MDA contained therein, up to 85 mass-%, preferably 30 mass- to 70 mass-%, and particularly preferably 35 mass-% to 65 mass-% MMDA.

In step b) of the process according to the invention the acid catalyst is neutralized by adding a base and the reaction mixture is separated into an organic and an aqueous phase. The organic phase contains the di- and polyamines of the diphenylmethane series (MDA) and also non-reacted aniline. The reaction mixture containing the di- and polyamines of the diphenylmethane series is optionally neutralized with addition of water and/or aniline. According to the prior art the neutralization is usually performed at temperatures of, for example, 90° C. to 120° C. without addition of further substances. However, it can also be performed at another temperature level, for example in order to accelerate the degradation of interfering secondary products. For example, the hydroxides of the alkali and alkaline earth elements are suitable as bases. Aqueous NaOH is preferably used. The base used for neutralization is preferably used in amounts of greater than 100%, particularly preferably 105% to 120% of the amount required stoichiometrically for the neutralization of the used acid catalyst (see EP 1 652 835 A1). In the terminology of the present invention the term neutralization also includes a "super neutralization" into the alkaline range.

The organic phase containing di- and polyamines of the diphenylmethane series (MDA) and non-reacted aniline obtained in step b) is then preferably washed with water in step c), wherein, after separation of the washing water phase, an organic phase largely to completely freed from salts and comprising MDA (and excess aniline) is obtained. The process adopted for this purpose is preferably as described in DE-A-2549890, page 3. In the terminology of the present invention the term wash (as used by a person skilled in the art) thus always also includes the separation of the washing water phase once the mixing of the organic phase to be purified and washing water is complete.

The remaining organic phase containing MDA and aniline still contains water also once the washing water phase has been separated off. This can be attributed to a residual solubility of water in the organic phase; in addition, it may quite possibly be in practice—in particular on an industrial scale—that the phase separation does not run perfectly and a (small) fraction of washing water phase is carried into the further processing of the organic phase containing MDA and aniline. The same is true of course for the aqueous phase after the neutralization if the washing is omitted; here as well a (small) fraction of the aqueous phase remains in the organic phase containing MDA and aniline.

The further processing in step d) of the organic phase obtained in step b) or step c) ("crude MDA") is performed in accordance with the invention by distillation. During this processing the two product streams of the process according to the invention are obtained: an MDA stream (first product stream) and an MMDA stream (second product stream).

Step d) can be realized in a number of different variants, which will be explained in greater detail further below with reference to the appended drawings. A common feature of all variants is that a head stream containing aniline and water is firstly separated off in a distillation column from the organic phase from step b) or step c) that is to be processed, wherein the first product stream accumulates as sump product of this distillation column. This sump product contains PMDA in a fraction of from at least 25.0 mass-%, preferably 30.0 mass-% to 70.0 mass-% and particularly preferably 35.0 mass-% to 65.0 mass-%, in relation to the total mass of the sump product. The remainder to 100 mass-% comprises MMDA and optionally high-boiling secondary products. The composition of this stream, in particular the MMDA fraction and the ratio of PMDA to MMDA, can be easily determined by means of analytical methods known to a person skilled in the art, such as in particular HPLC or GC. Generally, the various methods provide the same results—within insignificant fluctuations; in the case of any doubt, the MMDA fraction determined by means of HPLC is decisive to the purpose of the present invention. (In order to determine the composition by means of HPLC, the MDA to be examined is separated into its constituents using a suitable chromatograph, for example by means of an HPLC 1260 from Agilent, by reverse-phase chromatography on a C 18 column by means of gradient elution with a ternary mixture of methanol, acetonitrile and water with use of a UV detector at a wavelength of 240 nm. The MMDA isomers are quantified with the aid of an external calibration.)

This distillation is preferably performed at a sump temperature in the range of from 180° C. to 260° C., electively achieved by an internal heat exchanger functioning as a heater-dryer with the purpose of drying (possibly supported by guiding through an inert gas, in particular nitrogen) and a head pressure in the range of from 5 mbar$_{(abs.)}$ to 300 mbar$_{(abs.)}$. The sump product obtained (first product stream) contains, as already mentioned, not only the PMDA but also substantially MMDA and is preferably cooled to a temperature in the range of 90° C. to 140° C. This mixture of PMDA and MMDA (=MDA) is fed to its further use, preferably the phosgenation into MDI known from the prior art. The head product obtained in this distillation consists substantially of aniline and water. At least some of this aniline preferably is fed back into step a).

Furthermore, step d) of the present invention comprises a stripping with steam so as to obtain a gaseous stream containing aniline, water and MMDA. This steam stripping can be performed in the distillation column already mentioned or in a downstream apparatus. In the latter case this apparatus is connected to the distillation column via a side drain. Stripping columns known to a person skilled in the art are suitable as apparatuses for steam stripping in this sense. These are preferably operated at a sump temperature in the range of from 180° C. to 250° C. and a head pressure in the range of from 30 mbar$_{(abs.)}$ to 300 mbar$_{(abs.)}$. In any case a gaseous stream containing aniline, water and MMDA accumulates and generally has a temperature in the range of from 180° C. to 250° C. and is at a pressure in the range of from 5 mbar$_{(abs.)}$ to 300 mbar$_{(abs.)}$.

The gaseous stream containing aniline, water and MMDA accumulating during the steam stripping is partially condensed in accordance with the invention. Suitable technical arrangements for this purpose, such as condensers, are known to a person skilled in the art. These arrangements can be integrated in distillation columns or can be designed as independent pieces of equipment and are preferably operated at a temperature in the range of from 120° C. to 210° C. and at a pressure in the range of from 5 mbar$_{(abs.)}$ to 300 mbar$_{(abs.)}$. During the partial condensation a liquid stream containing MMDA and water (and optionally aniline) and a gaseous stream containing aniline and water (and optionally MMDA) are obtained. This gaseous stream is preferably guided into the distillation for separation of aniline and water in the distillation column discussed further above.

In order to obtain the second product stream the liquid flow thus obtained containing MMDA and water is dried. This can be performed in principle in all ways commonly known to a person skilled in the art. In accordance with the invention it is preferred to strip the liquid stream from the partial condensation under heating, in particular at a temperature in the range of from 210° C. to 260° C., by guiding through an inert gas, in particular nitrogen. The drying of the liquid stream is preferably followed (immediately) by a cooling of the dried stream to a temperature in the range of from 90° C. to 140° C. In this way the second product stream containing at least 95 mass-%, preferably at least 97.0 mass-%, particularly preferably at least 98.0 mass-% MMDA, in relation to the total mass of this stream, is obtained as condensate. What remains is a gas phase which not only contains water and the used inert gas, but can also contain 2,2'-MMDA and 2,4'-MMDA as low-boiling constituents and is therefore optionally preferably guided into the distillation for separation of aniline and water in the distillation column discussed further above. The difference to 100 mass-% in this second product stream consists substantially of water, aniline and PMDA, wherein the PMDA fraction of the second product stream is preferably at most 4.0 mass-%, particularly preferably at most 3.0 mass-%, and very particularly preferably at most 2.0 mass-%, in relation to the total mass of the second product stream. This MMDA stream preferably contains 83.0 mass-% to 92.0 mass-% of 4,4'-diaminodiphenylmethane, 7.0 mass-% to 14 mass-% of 2,4'-diaminodiphenylmethane, and 0.2 mass-% to 0.8 mass-% of 2,2'-diaminodiphenylmethane, in each case in relation to the total mass of the MMDA isomers. The composition of the second product stream can be determined using the same analytical methods as described previously for the first product stream.

This MMDA stream prepared in accordance with the invention as second product stream is exceptionally suitable for various applications. The following potential uses of this MMDA stream are preferred:
- gas phase or liquid phase phosgenation to form MMDI
- ring hydrogenation to form $H_{12}$-MMDA
- hardener for epoxy varnishes and composites
- raw material for polyether ether ketone (PEEK)

Figure 2:
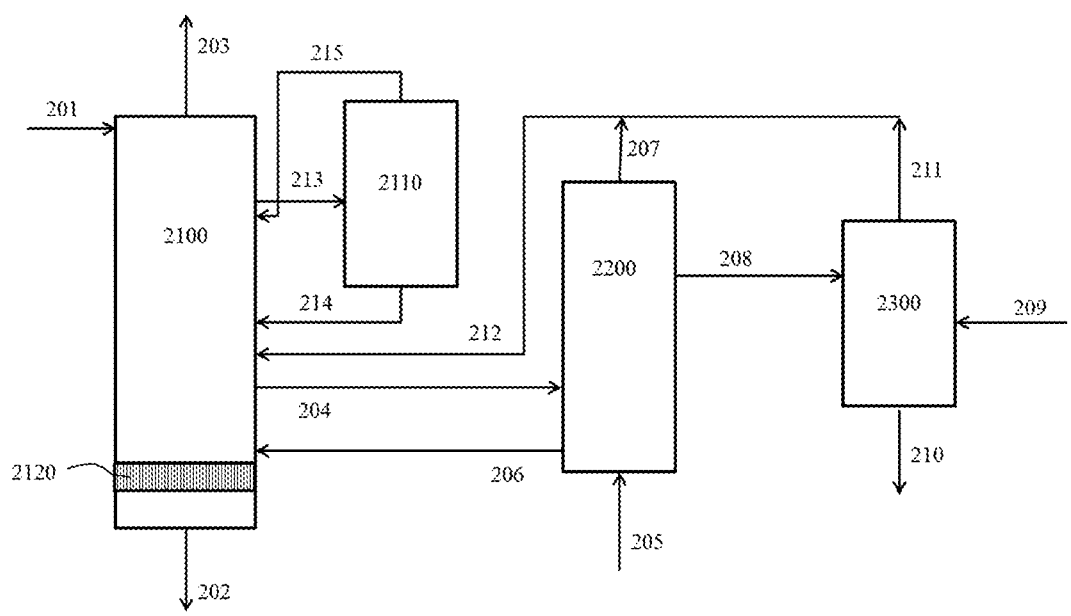
FIG. 2 shows a further possible embodiment of the process according to the invention with two distillation steps in the distillation columns 2100 and 2200.
Figure 3:
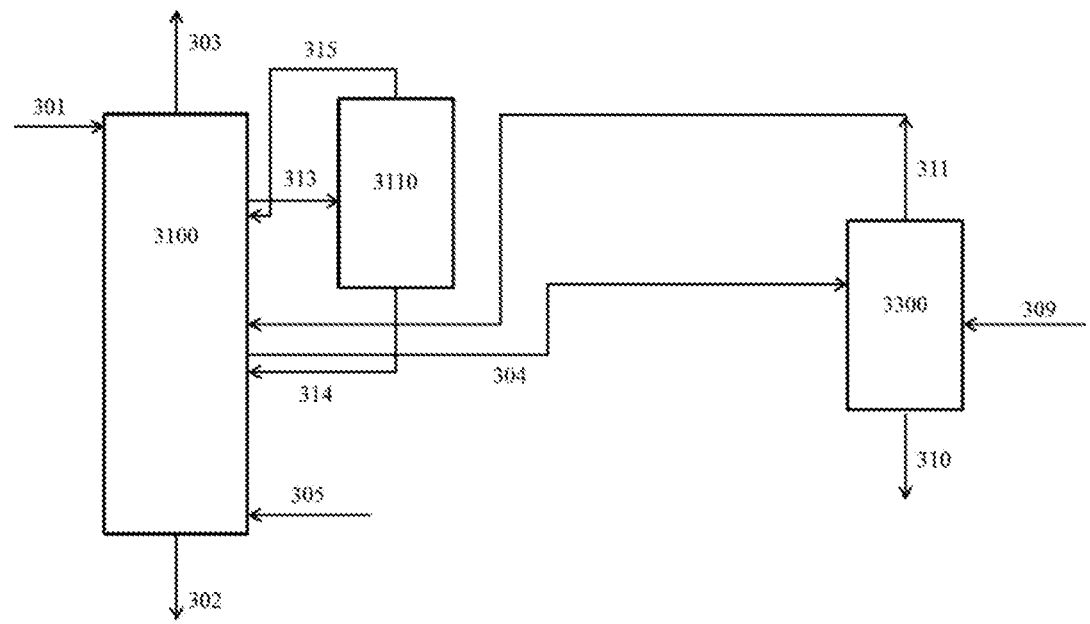
FIG. 3 shows a possible embodiment of the process according to the invention with a distillation step in the distillation column 3100.
Figure 4:
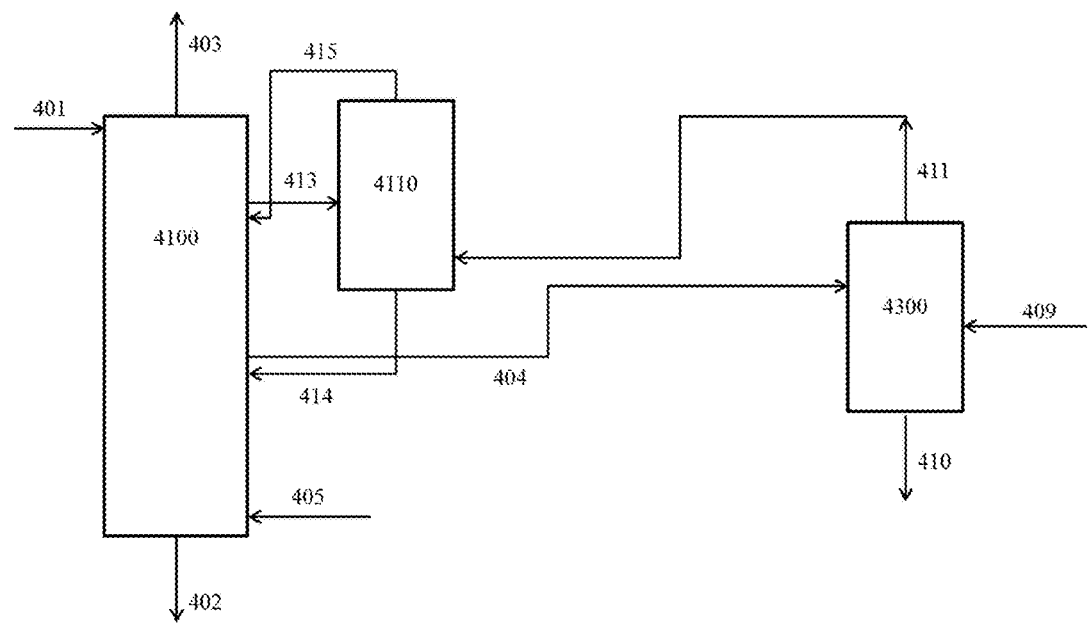
FIG. 4 shows a further possible embodiment of the process according to the invention with a distillation step in the distillation column 4100.
Figure 5:
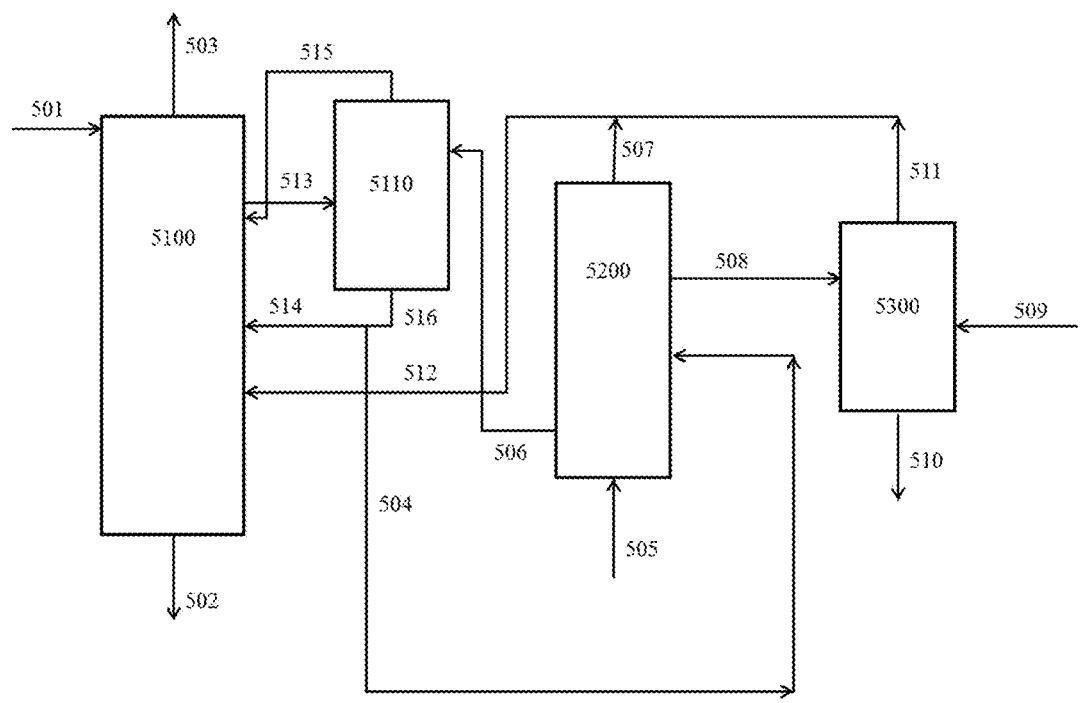
FIG. 5 shows a further possible embodiment of the process according to the invention with two distillation steps in the distillation columns 5100 and 5200.
Figure 6:
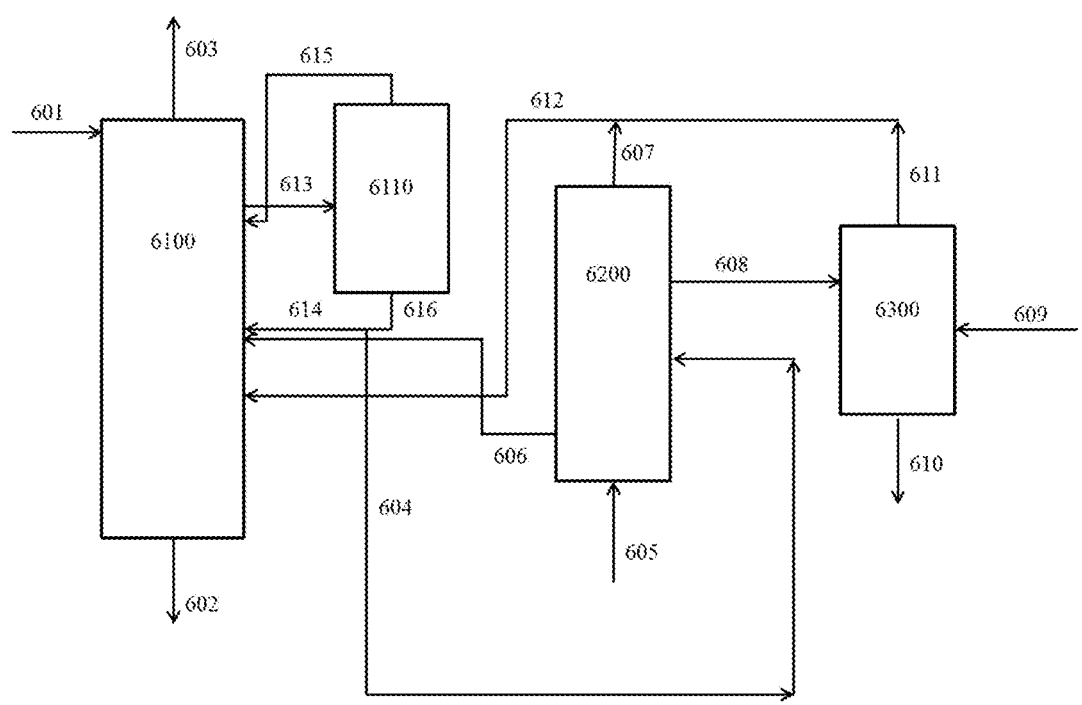
FIG. 6 shows a further possible embodiment of the process according to the invention with two distillation steps in the distillation columns 6100 and 6200.

Step d) of the process according to the invention will be explained in greater detail hereinafter with the aid of the appended drawings. In all of the drawings material streams have been denoted by three-digit numbers and pieces of equipment by four-digit numbers, wherein the first number in each case denotes the number of the figure and the following numbers are the same for like or comparable material streams or pieces of equipment. In the drawings:

FIG. 1 shows a possible embodiment of the process according to the invention with two distillation steps in the distillation columns 1100 and 1200;

FIG. 2 shows a further possible embodiment of the process according to the invention with two distillation steps in the distillation columns 2100 and 2200;

FIG. 3 shows a possible embodiment of the process according to the invention with a distillation step in the distillation column 3100;

FIG. 4 shows a further possible embodiment of the process according to the invention with a distillation step in the distillation column 4100;

FIG. 5 shows a further possible embodiment of the process according to the invention with two distillation steps in the distillation columns 5100 and 5200;

FIG. 6 shows a further possible embodiment of the process according to the invention with two distillation steps in the distillation columns 6100 and 6200;

and

Figure 7:
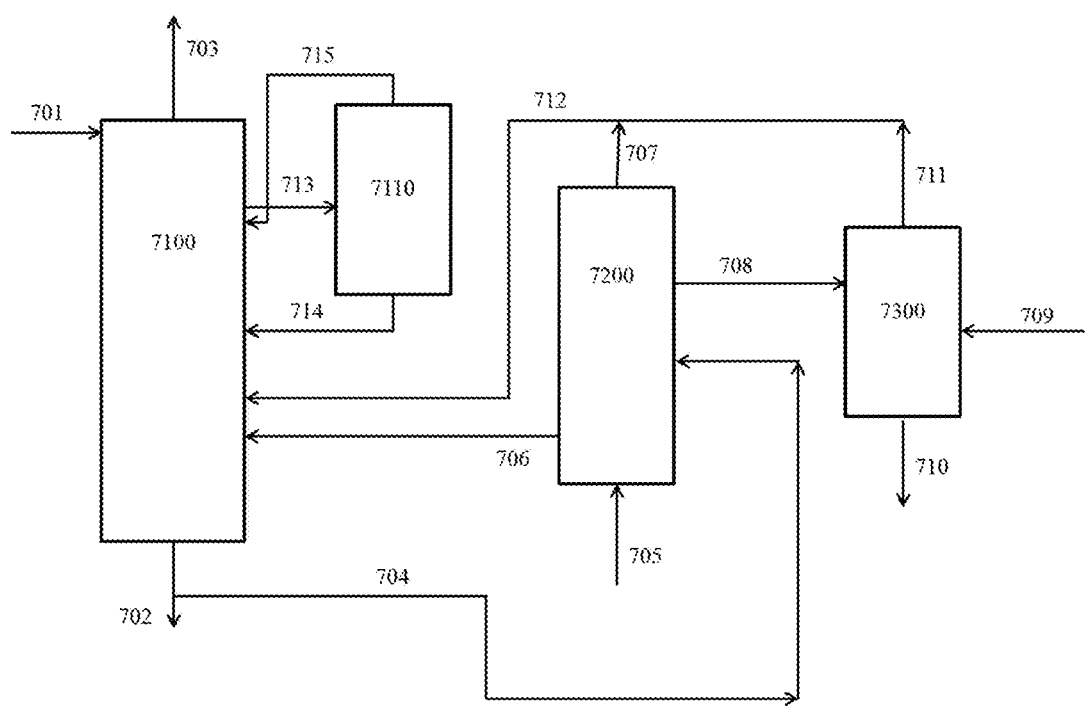
FIG. 7 shows a further possible embodiment of the process according to the invention with two distillation steps in the distillation columns 7100 and 7200.

FIG. 7 shows a further possible embodiment of the process according to the invention with two distillation steps in the distillation columns 7100 and 7200.

Overview of the pieces of equipment and most important material streams (X=number of the drawing):

| Equipment | | Material streams | |
|---|---|---|---|
| X100 | Distillation column (optionally with an internal heat exchanger X120 functioning as a heater-dryer in the lower region; a heat exchanger operated as a cooler (not shown) is situated in the column in the lower region thereof, below the heater-dryer if provided, or downstream of the column) | X01 | Crude MDA (organic phase containing MDA and aniline, inlet stream of the distillation process) |
| X110 | Evaporator | X02 | Sump product of the distillation column X100 (first product stream) |
| X200 | Distillation column (stripping column) | X03 | Head product (vapours) of the distillation column X100 containing aniline and water |
| X300 | Heater-cooler (comprising a heat exchanger operated as heater in the upper region and a heat exchanger operated as cooler in the lower region) | X04 | Stream removed as side drain of the distillation column X100 and containing PMDA, MMDA, aniline and water |
| | | X05 | Steam |
| | | X06 | Mixture containing MMDA drawn off in the lower region of the stripping column X200 |
| | | X07 | Vapours of the stripping column X200 containing aniline and water |
| | | X08 | Liquid stream containing MMDA and water and optionally aniline |
| | | X09 | Inert gas (in particular nitrogen) |
| | | X10 | MMDA stream obtained after cooling (second product stream) |
| | | X11 | Vapours of the heater-cooler X300 |
| | | X12 | Combined vapours of the stripping column X200 and of the heater-cooler X300 |
| | | X13 | Infeed stream of the evaporator X110 |
| | | X14 | Sump stream of the evaporator X110 |
| | | X15 | Vapours of the evaporator X110 |

FIG. 1 shows a possible embodiment of the process according to the invention:

An MDA stream 101 (the organic phase obtained in step b) or step c)) is conducted into a distillation column 1100. The stream 103 containing aniline and water is removed at the head of this column. The distillation column 1100 has, in the lower region, a heat exchanger 1120 functioning as a heater-dryer for generating the first product stream, which is drawn off in the sump as stream 102. A mixture 104 containing MMDA is drawn off below the heater-dryer 1120 as side stream and is fed laterally into a stripping column 1200. The distillation column 1100 has an evaporator 1110, which is fed from the distillation column via a side drain 113, which lies below the feed of the stream 101. The sump discharge 114 and vapour stream 115 of the evaporator are guided back into the distillation column 1100; more specifically the vapour stream 115 below the side drain 113 and the sump stream 114 above the side drain 104 and below the vapour stream 115.

Steam 105 is guided through the stripping column 1200 from bottom to top. In the lower region of the stripping column 1200 a mixture 106 containing MMDA and PMDA is drawn off and is fed back into the column 1100 above the heater-dryer and below the sump stream 114. In the upper region of the stripping column 1200 there is a condenser (not shown) for partially condensing the upwardly rising gas mixture. At the head of the stripping column 1200 the non-condensed vapours 107 containing aniline and steam (and also containing MMDA) are drawn off. In a side removal point of the stripping column 1200 arranged below the condenser and above the feed of the stream 104, a liquid stream 108 comprising aniline, water and MMDA is removed. This stream 108 is stripped dry in the upper region of the heater-cooler 1300 whilst guiding through an inert gas 109 (in particular nitrogen) under heating. The inert gas 109 is fed laterally below the feed of the stream 108. The liquid phase dried in this way is cooled in the lower region of the heater-cooler 1300 and is discharged at the sump drain as second product stream. The vapour stream 111 removed from the heater-cooler comprises water, the used inert gas (in particular nitrogen) and MMDA (and optionally aniline not separated with stream 107). The vapour streams from 1200 and 1300 are combined to form the stream 112. This stream 112 is fed to the column 1100 above the stream 106 and below the stream 114 and is likewise used as stripping gas, in particular due to its high steam fraction.

FIG. 2 shows a possible embodiment of the process according to the invention:

In the variant according to FIG. 2, in contrast to the variant according to FIG. 1, the mixture 204 containing MMDA is drawn off above the heater-dryer 2120 of the distillation column 2100 (which results in an increased water content as compared to the stream 204). The mixture 206 containing MMDA and PMDA drawn off in the lower region of the stripping column is fed back into the column 2100 above the heater-dryer.

FIG. 3 shows a further possible embodiment of the process according to the invention:

In this variant the stripping with steam 305 is performed in the distillation column 3100 and an additional stripping column therefore can be spared. In contrast to the variants according to FIGS. 1 and 2, here the sump stream 314 of the evaporator 3110 is fed back into the distillation column 3100 below the side drain 304, which for its part is arranged below the vapour stream 311. In this variant it is possible to provide a condenser above the side drain 304 for partially liquefying the rising gas phase so that the stream 304 is removed in liquid form. In this case the piece of equipment 3300 functions as a heater-cooler and is operated as in the variants according to FIGS. 1 and 2. It is also possible, however, to remove the stream 304 of the distillation column 3100 in gaseous form and to carry out the partial condensation outside this distillation column. In this case the stream 304 must then pass through a condenser (not shown) before the drying by inert gas stripping, said condenser being arranged either outside 3300 or in 3300 above the heat exchanger operated as a heater.

FIG. 4 shows a further possible embodiment of the process according to the invention:

This variant corresponds to the variant according to FIG. 3 with the difference that the vapour stream 411 is not guided into the distillation column 4100, but into the evaporator 4110.

FIG. 5 shows a further possible embodiment of the process according to the invention:

In this variant the stripping with steam 505 is performed as in the variants according to FIGS. 1 and 2 in a stripping column 5200. In contrast to these two variants the infeed stream for the stripping column 504 originates from the sump drain of the evaporator 5110, of which only a part is fed back as stream 514 into the distillation column 5100. In other words, in this variant the stripping column 5200 is connected via the "intermediate" evaporator 5110 to a side drain of the distillation column 5100, specifically 513. The mixture 506 containing MMDA and PMDA is guided into the evaporator 5110.

FIG. 6 shows a further possible embodiment of the process according to the invention:

The variant according to FIG. 6 corresponds to that from FIG. 5 with the difference that the mixture 606 containing MMDA and PMDA is not guided into the evaporator 6110, but, similarly to the variant according to FIG. 1, is guided into the distillation column 6100 between the stream 614 and the stream 612.

FIG. 7 shows a further possible embodiment of the process according to the invention:

In contrast to the previous variants, here the stripping column (7200) is fed not from a side stream of the distillation column (7100), but from a partial stream (704) branched off from the sump stream of the distillation column. Otherwise, the positioning of the column corresponds to the embodiment according to FIG. 1.

The invention claimed is:

1. A process for the preparation of di- and polyamines of the diphenylmethane series, comprising:
　a) subjecting aniline and formaldehyde to acid catalyzed condensation so as to obtain an acidic process product containing water, di- and polyamines of the diphenylmethane series (MDA), and aniline;
　b) neutralizing the acidic process product followed by separation of the neutralized process product into an organic phase containing MDA and aniline and an aqueous phase;
　c) optionally, washing the organic phase containing MDA and aniline;
　d) treating the organic phase containing MDA and aniline to obtain a first product stream containing, in relation to its total mass, at least 25.0 mass-% of polyamines of the diphenylmethane series (PMDA), wherein the remainder comprises the diamines of the diphenylmethane series, and a second product stream containing, in relation to its total mass, at least 95.0 mass-% of diamines of the diphenylmethane series (MMDA), wherein the treatment comprises:
　　in a distillation column, separating off, from the organic phase containing MDA and aniline, a stream containing aniline and water as head product to obtain the first product stream as sump product, wherein the separating off of the stream containing aniline and water further comprises a stripping with steam to obtain a gaseous stream that is separate from the head product containing aniline, water and MMDA, the stripping with steam being performed either:
　　(1) by introducing steam into said distillation column, or (2) by withdrawing a stream containing PMDA, MMDA, aniline and water from said distillation column and stripping said stream containing PMDA, MMDA, aniline and water in an apparatus arranged downstream of said distillation column partially condensing the gaseous stream containing aniline, water and MMDA obtained by the stripping with steam to obtain a liquid stream containing MMDA and water and a gaseous stream containing aniline and water, and drying the liquid stream containing MMDA and water obtained by the partial condensation to obtain the second product stream.

2. The process of claim 1, in which the first product stream contains 30.0 mass-% to 70.0 mass-% of polyamines of the diphenylmethane series and the second product stream contains at least 97.0 mass-% of diamines of the diphenylmethane series.

3. The process of claim 2, in which the first product stream contains 35.0 mass-% to 65.0 mass-% of polyamines of the diphenylmethane series and the second product stream contains at least 98.0 mass-% of diamines of the diphenylmethane series.

4. The process of claim 1, in which in step a) a molar ratio of total aniline used to the total formaldehyde used is at least 1.6.

5. The process of claim 1, in which step c) is included.

6. The process of claim 1, in which the stripping with steam is performed in the distillation column.

7. The process of claim 1, in which the stripping with steam is performed in an apparatus arranged downstream of the distillation column.

8. The process of claim 7, in which the apparatus arranged downstream of the distillation column is a packed column.

9. The process of claim 7, in which the apparatus arranged downstream of the distillation column is connected to a side drain of the distillation column, optionally via an intermediate piece of equipment.

10. The process of claim 9, in which the intermediate piece of equipment is included.

11. The process of claim 10, in which the intermediate piece of equipment is an evaporator.

12. The process of claim 7, in which some of the sump product of the distillation column is conducted into the apparatus arranged downstream of the distillation column.

13. The process of claim 1, in which drying the liquid stream containing MMDA and water in step d) is performed with an inert gas under heating.

14. The process of claim 13, in which in step d) a cooling is performed after the drying.

15. The process of claim 13, in which the inert gas used for drying comprises nitrogen.

* * * * *